(12) United States Patent
Thienphrapa et al.

(10) Patent No.: US 11,602,403 B2
(45) Date of Patent: Mar. 14, 2023

(54) ROBOTIC TOOL CONTROL

(71) Applicant: KONINKLIJKE PHILIPS N.V., Eindhoven (NL)

(72) Inventors: Paul Thienphrapa, Cambridge, MA (US); Molly Lara Flexman, Melrose, MA (US); Torre Michelle Bydlon, Melrose, MA (US); Aleksandra Popovic, Boston, MA (US); Marcin Arkadiusz Balicki, Cambridge, MA (US); Grzegorz Andrzej Toporek, Boston, MA (US); Alexandru Patriciu, Belmont, MA (US)

(73) Assignee: KONINKLIJKE PHILIPS N.V, Eindhoven (NL)

( * ) Notice: Subject to any disclaimer, the term of this patent is extended or adjusted under 35 U.S.C. 154(b) by 374 days.

(21) Appl. No.: 16/762,333

(22) PCT Filed: Nov. 13, 2018

(86) PCT No.: PCT/EP2018/080999
§ 371 (c)(1),
(2) Date: May 7, 2020

(87) PCT Pub. No.: WO2019/092261
PCT Pub. Date: May 16, 2019

(65) Prior Publication Data
US 2021/0068908 A1    Mar. 11, 2021

Related U.S. Application Data

(60) Provisional application No. 62/585,021, filed on Nov. 13, 2017.

(51) Int. Cl.
*A61B 34/35* (2016.01)
*A61B 34/32* (2016.01)
(Continued)

(52) U.S. Cl.
CPC .............. *A61B 34/35* (2016.02); *A61B 34/32* (2016.02); *A61B 34/77* (2016.02); *A61B 90/361* (2016.02);
(Continued)

(58) Field of Classification Search
CPC ......... A61B 34/35; A61B 34/32; A61B 34/77; A61B 90/361; A61B 2034/301;
(Continued)

(56) References Cited

U.S. PATENT DOCUMENTS 5,762,458 A * 6/1998 Wang ..................... A61B 34/71
606/130
5,894,843 A * 4/1999 Benetti .................. A61B 90/00
606/190

(Continued)

FOREIGN PATENT DOCUMENTS

EP          1150601        11/2001
WO       2008/086430        7/2008

OTHER PUBLICATIONS

International Search Report and Written Opinion dated Feb. 20, 2019 for International Application No. PCT/EP2018/080999 Filed Nov. 13, 2018.

(Continued)

*Primary Examiner* — Jaime Figueroa

(57) ABSTRACT

A system for controlling a robotic tool includes a memory that stores instructions and a processor that executes the instructions. When executed by the processor, the instructions cause the system to perform a process that includes monitoring sequential motion of tissue in a three-dimensional space. The process also includes projecting locations and corresponding times when the tissue will be at projected locations in the three-dimensional space. An identified location of the tissue in the three-dimensional space is identified (Continued)

based on the projected locations. A trajectory of the robotic tool is set to meet the tissue at the identified location at a projected time corresponding to the identified location.

15 Claims, 10 Drawing Sheets

(51) Int. Cl.
  *A61B 34/00* (2016.01)
  *A61B 90/00* (2016.01)
  *A61B 34/30* (2016.01)
(52) U.S. Cl.
  CPC ... *A61B 2034/301* (2016.02); *A61B 2090/367* (2016.02)
(58) Field of Classification Search
  CPC ... A61B 2090/367; A61B 90/36; A61B 34/30; A61B 2017/00694
  USPC ............................... 606/130; 700/245–264; 318/568.11–568.25
  See application file for complete search history.

(56) References Cited

U.S. PATENT DOCUMENTS

| | | | | |
|---|---|---|---|---|
| 5,923,770 | A * | 7/1999 | O'Donnell | G06T 7/251 600/416 |
| 8,708,902 | B2 * | 4/2014 | Heimbecher | A61B 5/7425 600/300 |
| 8,784,290 | B2 * | 7/2014 | Sumanaweera | A61N 5/1039 600/1 |
| 9,320,916 | B2 * | 4/2016 | Sumanaweera | A61B 6/037 |
| 9,788,910 | B2 * | 10/2017 | Schuh | A61B 5/6852 |
| 10,874,468 | B2 * | 12/2020 | Wallace | A61B 34/37 |
| 2007/0013336 | A1 * | 1/2007 | Nowlin | A61B 34/37 318/568.21 |
| 2008/0177280 | A1 | 7/2008 | Adler | |
| 2011/0166407 | A1 * | 7/2011 | Sumanaweera | A61N 5/1077 600/1 |
| 2012/0087563 | A1 | 4/2012 | Ionasec | |
| 2012/0173217 | A1 * | 7/2012 | Heimbecher | A61B 34/20 703/11 |
| 2013/0131425 | A1 * | 5/2013 | Sumanaweera | A61N 5/1037 600/1 |
| 2014/0005684 | A1 * | 1/2014 | Kim | G16H 20/40 606/130 |
| 2021/0393331 | A1 * | 12/2021 | Hufford | A61B 1/018 |

OTHER PUBLICATIONS

Loschak, et al: "Predictive filtering in motion compensation with steerable cardiac catheters", 2017 IEEE International Conference on Robotics and Automation, May 29, 2017.

Ginhoux, et al: "Active Filtering of Physiological Motion in Robotized Surgery Using Predictive Control", IEEE Transactions on Robotics, vol. X, No. Y, Nov. 2003.

"Ultrasound-Based Image Guidance and Motion Compensating Control for Robot-Assisted Beating-Heart Surgery", Journal of Medical Robotics Research, vol. 1, No. 1 (2016) 1640002 (11 pages).

Bebek, et al: "Intelligent Control Algorithms for Robotic Assisted Beating Heart Surgery", Regular Paper Submission for the IEEE Transactions on Robotics.

* cited by examiner

Linear (XYZ)
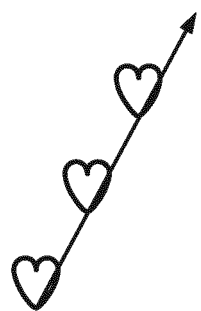
FIG. 7A
Rotational RΘΦ
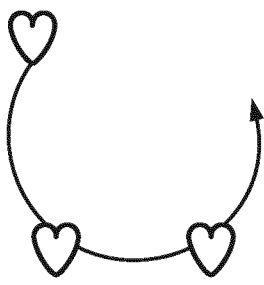
FIG. 7B
Rhythmic
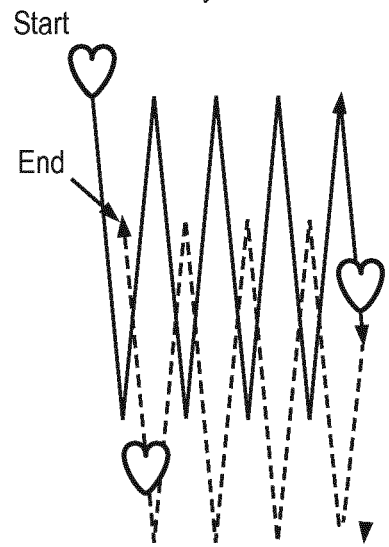
FIG. 7C
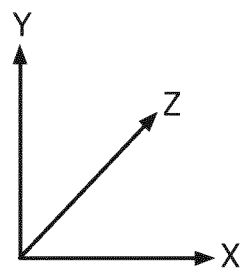
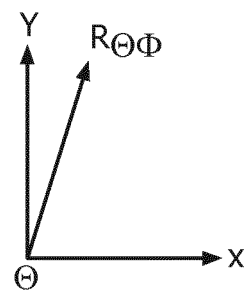
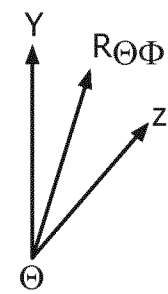

Position/time data from monitoring

| T1 | X1 | Y1 | Z1 | R1 | Θ1 | Φ1 |
|---|---|---|---|---|---|---|
| T2 | X2 | Y2 | Z2 | R2 | Θ2 | Φ2 |
| T3 | X3 | Y3 | Z3 | R3 | Θ3 | Φ3 |
| T4 | X4 | Y4 | Z4 | R4 | Θ4 | Φ4 |
| T5 | X5 | Y5 | Z5 | R5 | Θ5 | Φ5 |
| T6 | X6 | Y6 | Z6 | R6 | Θ6 | Φ6 |
| T7 | X7 | Y7 | Z7 | R7 | Θ7 | Φ7 |
| T8 | X8 | Y8 | Z8 | R8 | Θ8 | Φ8 |
| T9 | X9 | Y9 | Z9 | R9 | Θ9 | Φ9 |
| T10 | X10 | Y10 | Z10 | R10 | Θ10 | Φ10 |
| T11 | X11 | Y11 | Z11 | R11 | Θ11 | Φ11 |
| T12 | X12 | Y12 | Z12 | R12 | Θ12 | Φ12 |
| T13 | X13 | Y13 | Z13 | R13 | Θ13 | Φ13 |
| T14 | X14 | Y14 | Z14 | R14 | Θ14 | Φ14 |
| T15 | X15 | Y15 | Z15 | R15 | Θ15 | Φ15 |
| T16 | X16 | Y16 | Z16 | R16 | Θ16 | Φ16 |
| T17 | X17 | Y17 | Z17 | R17 | Θ17 | Φ17 |
| T18 | X18 | Y18 | Z18 | R18 | Θ18 | Φ18 |
| T19 | X19 | Y19 | Z19 | R19 | Θ19 | Φ19 |
| T20 | X20 | Y20 | Z20 | R20 | Θ20 | Φ20 |
| T21 | X21 | Y21 | Z21 | R21 | Θ21 | Φ21 |
| T22 | X22 | Y22 | Z22 | R22 | Θ22 | Φ22 |
| T23 | X23 | Y23 | Z23 | R23 | Θ23 | Φ23 |
| T24 | X24 | Y24 | Z24 | R24 | Θ24 | Φ24 |
| T25 | X25 | Y25 | Z25 | R25 | Θ25 | Φ25 |

FIG. 9

ROBOTIC TOOL CONTROL

CROSS REFERENCE TO RELATED APPLICATIONS

This application is the U.S. National Phase application under 35 U.S.C. § 371 of International Application No. PCT/EP2018/080999 filed Nov. 13, 2018, published as WO 2019/092261 on May 16, 2019, which claims the benefit of U.S. Provisional Patent Application No. 62/585,021 filed Nov. 13, 2017. These applications are hereby incorporated by reference herein.

BACKGROUND

Minimizing aspects of invasive surgery on a beating heart can produce benefits such as reducing trauma and avoiding cardiopulmonary bypass. Heart surgery is typically performed in a confined and dynamic environment. As a result, efforts to minimize the invasiveness of heart surgery encounter challenges to navigation around the heart, visualization of the heart and the environment around the heart, and manipulation of the heart and tools used to perform the heart surgery.

Motion relating to the heart and lungs is known as cardiopulmonary motion, and such motion is relatively predictable. Accordingly, conventional practices for heart surgery have focused on motion compensation capabilities that allow a robot to synchronize movements with the tissue, thereby freeing a medical professional (e.g., surgeon) from having to cognitively and manually handle heartbeat motion manually. However, when the tissue moves in more than one degree of freedom, the conventional mechanical motion compensation capabilities may not track the tissue faithfully.

Another aspect of heart surgery is that the procedures may sometimes involve manipulating moving tissue continuously. However, some procedures do not require such continuous manipulation of moving tissue. Examples of procedures that may not require continuous manipulation of moving tissue include mitral valve repair and patent foramen ovale closure.

SUMMARY

According to an aspect of the present disclosure, a system for controlling a robotic tool includes a memory that stores instructions; and a processor that executes the instructions. When executed by the processor, the instructions cause the system to perform a process including monitoring sequential motion of tissue in a three-dimensional space, and projecting locations and corresponding times when the tissue will be at projected locations in the three-dimensional space. An identified location of the tissue in the three-dimensional space is identified based on the projected locations. A trajectory of the robotic tool is set to meet the tissue at the identified location at a projected time corresponding to the identified location.

According to another aspect of the present disclosure, a method for controlling a robotic tool includes monitoring sequential motion of tissue in a three-dimensional space. The method includes projecting, by a tangible and non-transitory processor, locations and corresponding times when the tissue will be at projected locations in the three-dimensional space. The method further includes identifying an identified location of the tissue in the three-dimensional space based on the projected locations and at least one characteristic of a robotic tool. A trajectory of the robotic tool is set to meet the tissue at the identified location at a projected time corresponding to the identified location. The robotic tool or a medical therapy device attached to the robotic tool is deployed to meet the tissue at the identified location along the trajectory.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIG. 7A illustrates a simplified form of tissue motion monitored in robotic tool control, in accordance with a representative embodiment.

FIG. 7B illustrates another simplified form of tissue motion monitored in robotic tool control, in accordance with a representative embodiment.

FIG. 7C illustrates another simplified form of tissue motion monitored in robotic tool control, in accordance with a representative embodiment.

FIG. 9 illustrates data obtained from monitoring tissue motion for robotic tool control, in accordance with a representative embodiment.

DETAILED DESCRIPTION

Figure 1:
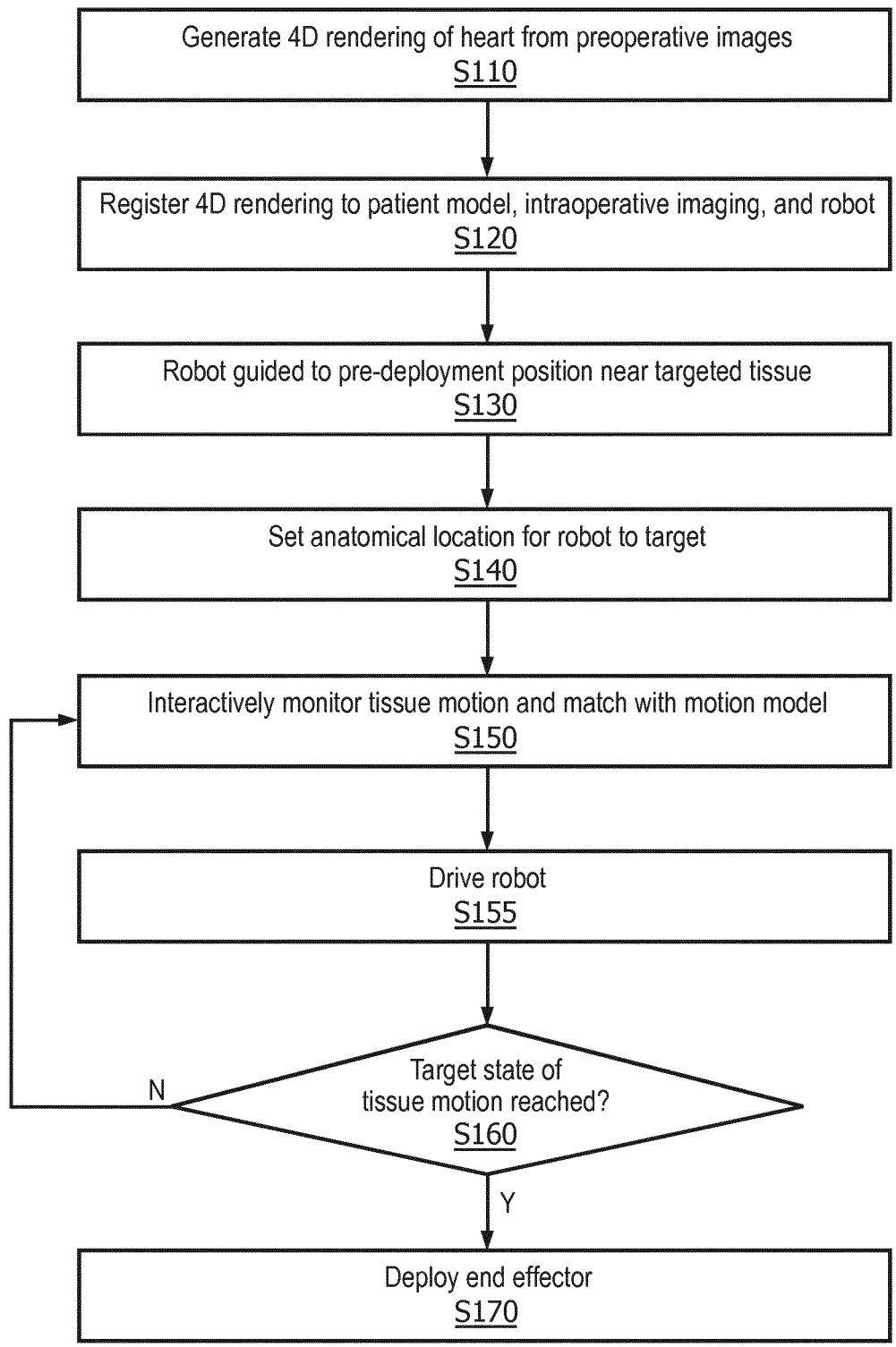
FIG. 1 illustrates a process for robotic tool control, in accordance with a representative embodiment.

A surgical system is described herein. The surgical system exploits the idea that a robot may only need to interact with moving tissue of a heart for an instant, such as for one heartbeat, for a variety of procedures. A robot control strategy for the surgical system monitors tissue motion from the heartbeat, and may monitor tissue motion from other sources such as respiration. The robot control strategy integrates patterns identified from the tissue motion to a control loop such that a desired trajectory, as defined by the user or the task, is matched in accordance with the timing of the tissue motion. The matching up of heartbeat-based tissue motion to robotic control may be made invisible to the operator, so that the operator need only specify a tissue target, and the robot computes the requisite trajectory and timing to execute the deployment. Accordingly, cognitive load on the medical professional is reduced, and the operation simplified.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

As described herein, for some heart surgery procedures such as mitral valve repair, a robot can grasp at target tissue to reduce or stop the tissue movement, thereby securing the tissue for further manipulation. By reducing or stopping the tissue movement, even for only a moment, the robot can reduce reliance on the integrity of motion compensation. As an alternative to grasping at target tissue, the robot may simply deploy a device that attaches to the target tissue. Whether grasping the target tissue, deploying a device, or performing any other procedure that can be performed quickly, the robot need only accommodate heartbeat motion for a single interval of time. As a result, continuous motion compensation is technologically excessive and requires that a robot comprise mechanisms of greater performance, precision, complexity, and cost. The robotic tool control described herein may be used by itself without continuous motion compensation, or by a system that selectively uses the robotic tool control for one or more processes while also using continuous motion compensation for other processes.

FIG. 1 illustrates a process for robotic tool control, in accordance with a representative embodiment. In FIG. 1, the process starts at S110 when a 4-dimensional (4D) rendering of a heart is generated based on preoperative images. 4 dimensional, as the term is used herein, refers to a sequence of 3-dimensional (3D) renderings obtained over time, so that time is the 4th dimension. Preoperative images are images of a patient prior to an operation, and may include images taken immediately before the operation, as well as images taken long before the operation at a different site than the site of the operation. Additionally, while the rendering of the heart at S110 can be useful, the rendering of the heart at S110 is not particularly required for the robotic tool control described herein to function properly.

At S120, the 4-dimensional rendering is registered to a patient model, intraoperative imaging and a robot. A patient model is information specific to a patient in, for example, a predetermined format. The 4-dimensional rendering may be part of the patient model or simply correlated with the patient model. Intraoperative imaging is imaging of a patient during an operation, such as by ultrasound or X-ray. The 4-dimensional rendering may be used for comparison with intraoperative images so as to determine or confirm aspects of a patient's physiology encountered during the operation. A robot is a medical robot that moves in 1, 2 or 3 positional dimensions and in 1, 2, or 3 rotational dimensions in order to move robotic tools and/or commercial therapy devices in space as part of an operation. An example of a commercial therapy device is a medical therapy device.

At S130, the robot is guided to a pre-deployment position near targeted tissue. The particular tissue may not yet be identified, so the pre-deployment position may be a default pre-mapped site in the 3-dimensional operative space. The 3-dimensional operative space may be provided with an origin, so that the robot and all information can be mapped relative to the same origin with directional axes also predefined. The robot may be guided automatically or by hand. Automatic guidance may be performed by a computer executing a program based on the intraoperative images obtained during the operation. Hand guidance may be performed by an operator using, for example, a joystick, touch screen, roller ball, or other form of touch input.

At S140, an anatomical location for a robot to target is set. The anatomical location may be a specific part of tissue identified by pathology or other clinical characteristics, color or other visual characteristics, or by positioning relative to other anatomical locations. The other anatomical locations may be considered a form of anatomical landmarks. The anatomical locations may also be selected by the medical professional from images, or automatically by surgical system from the images using the anatomical landmarks, or by using characteristics of the tissue to be targeted such as force values from a force sensor or optical readings from an optical sensor. The anatomical location may be set automatically by a computer such as the computer executing the program based on the intraoperative images, though when set automatically the location should be confirmed by a medical professional. Alternatively, the anatomical location for the robot to target may be set by a medical professional, such as by the operator using the joystick, touch screen, roller ball, or other form of touch input.

As an alternative to using images, tissue motion may also be sensed through sensing that does not necessarily include imaging. For example, tissue motion information may be obtained through range sensing, pressure sensing, electrical (e.g., capacitance) sensing, and so on. Any form of sensing of tissue motion may be used to supplement or replace the intraoperative images described herein.

At S150, tissue motion is interactively monitored and then matched with a motion model. Tissue motion may include multiple forms of motion including heartbeat motion, respiratory motion, physical motion caused by the patient moving muscles, and/or feedback motion caused by the patient being moved in response to previous movement by the robot. The motion may be motion of one or more parts of an organ in different directions, including XYZ motion and rotational motion. Additionally, the motion may include multiple different components in any direction or rotation. For example, an overall heart may be moving at a measured pace while a particular tissue of the heart is moving at an offset from the measured pace. As an analogy, a particular tissue of the heart may move in a way partly similar to a circus ride, where arms rotate about an axis, the arms move up and down while rotating about the axis, and cars rotate at the ends of the arms about different axes formed at the end of each arm. Of course, tissue of a heart does not include the full range of such analogous motions, but the different degrees of motion may be similar. Tissue motion monitored at S150 may be monitored by a variety of mechanisms, including electrocardiogram (ECG), live imaging, a predetermined model that is synchronized to live patient physiological signals, or some hybrid thereof. The heart tissue may be marked and monitored in 3 dimensions.

Additionally, multiple motion models may be pre-registered and stored in a memory. For example, different tissue motions that have been identified as corresponding to different symptoms or diseases may be pre-registered as different motion models. The motion models may also correspond with patient age and gender as well as demographic and heath characteristics of the patient. Alternatively, the motion models may be entirely independent of demographic and health characteristics of the patient, and may correspond specifically only to types and patterns of tissue motions that are observed.

At S155, the robot is driven along a trajectory to meet the tissue at the identified location. The robot may be driven from the pre-deployment position reached at S130. The driving of the robot may occur in several ways/modes. That is, the intended result of the process in FIG. 1 is that a robotic end effector is deployed, as described below with respect to S170. When the robot meets the tissue, the deployment of the robotic end effector may take many forms such as grasping the tissue, installing (e.g., attaching, affixing) a device, cutting the tissue, and so on. The trajectory itself may reflect several considerations including meeting the targeted heart tissue, avoiding collisions with other tissue and any other objects in the 3-dimensional operational space, and velocity and directional considerations to minimize or entirely avoid the possibility of harming the patient if the trajectory is invalidated by unexpected behavior of the patient.

The position at which the robotic end effector is deployed may be a single optimal position that is determined in accordance with predetermined criteria. For example, an optimal position for a robotic tool to intercept heart tissue may be a position where motion of the heart tissue is at a positional extremity and/or a velocity minimum. Alternatively, an optimal position of heart tissue may be the patient is done exhaling and will begin inhaling. Thus, an optimal position may correspond to physiological characteristics of the patient in the operation, and these physiological characteristics may be dynamically determined in real time. Alternatively, an optimal position may correspond to characteristics of the tissue motion, and these motion characteristics may also be dynamically determined in real time. Moreover, the optimal position may correspond to an optimal time, wherein the timing is the primary consideration rather than the position. This may be true for setting positions based on respiratory timing, for example.

The position at which the robotic end effector is deployed may also be a preferred position among a set of multiple optimal positions, such as when multiple positions meet a minimum threshold for identifying potential interception locations. A preferred position may be determined randomly from a set of feasible positions, may be designated from a set of feasible positions by the medical professional, or may be determined in accordance with user settings of the medical professional such as if a surgeon is left handed or right handed.

Figure 5:
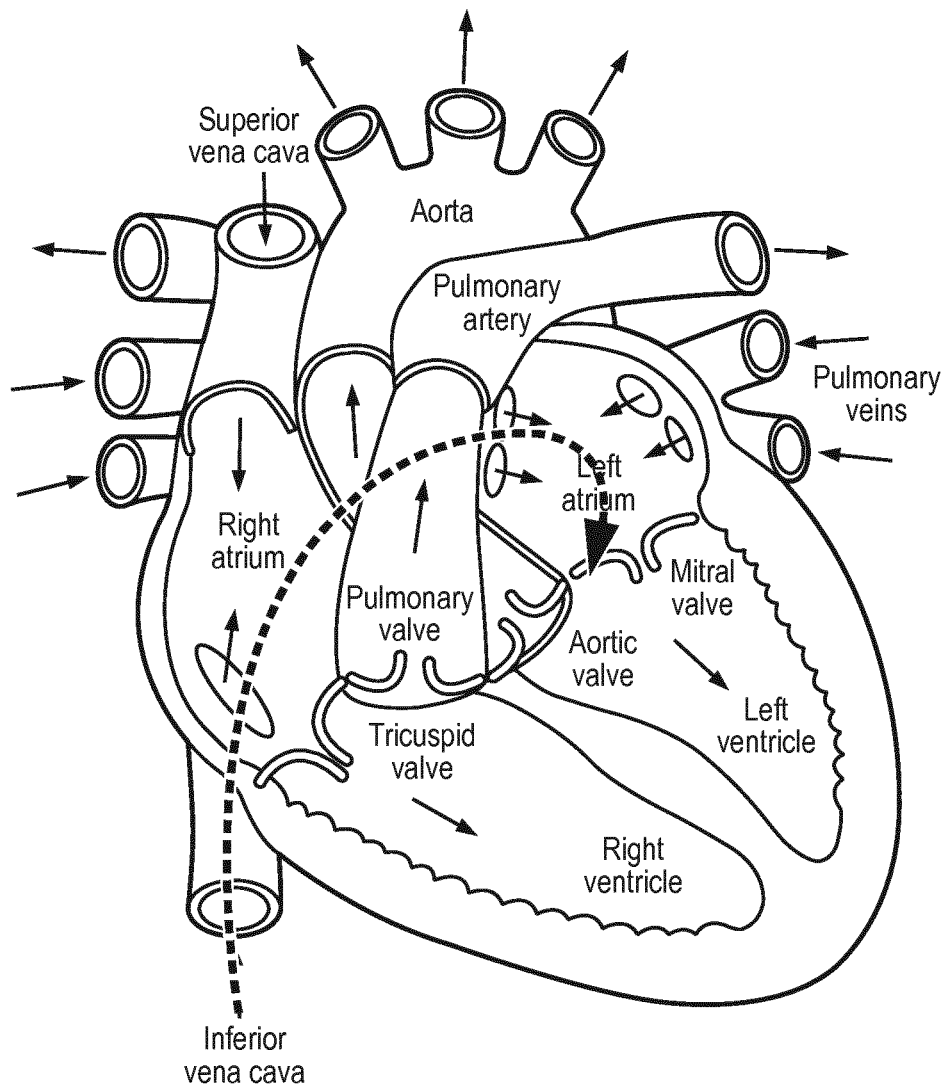
FIG. 5 illustrates the heart of FIG. 4 with a proposed trajectory of a robotic tool for robotic tool control, in accordance with a representative embodiment.

In a first mode of teleoperated deployment, the medical professional may use an input device or devices to move the robot towards the target tissue, and the surgical system implicitly uses heartbeat timing signals to constrain the real motion along a trajectory. The constraints may limit both velocity and location of the movement, even though the use of heartbeat timing signals to constrain motion may be performed invisibly or subtly to the medical professional such that the medical professional does not sense the constraint being imposed. In a second mode of autonomous deployment, a medical professional may specify to the surgical system the target tissue, and the surgical system executes the movement autonomously. In the second mode, the system can select the optimal timing and trajectory for the deployment of the robotic end effector. Additionally, as shown in FIG. 5, the surgical system may present a simulated view of what the deployment may look like for confirmation from the medical professional.

At S160, a determination is made whether the target state of the tissue motion is reached. The target stage may be, for example, a particular position in 3D, and/or a velocity and direction or trajectory of motion for the tissue. If the tissue is not in the expected state, the process of FIG. 1 may be restarted. The determination may be made by comparing the intraoperative images with the 4D rendering in real time, or by marking the tissue with, for example, a dye, so that the determination at S160 can be made visually by the medical professional. If the target position is not reached (S160=No), the process returns to S150 and the interactive monitoring of tissue motion is again performed.

If the target position is reached (S160=Yes), an end effector is deployed at S170. An end effector may be a robotic tool or a commercial therapy device such as a mitral clip or a valve.

Figure 2A:
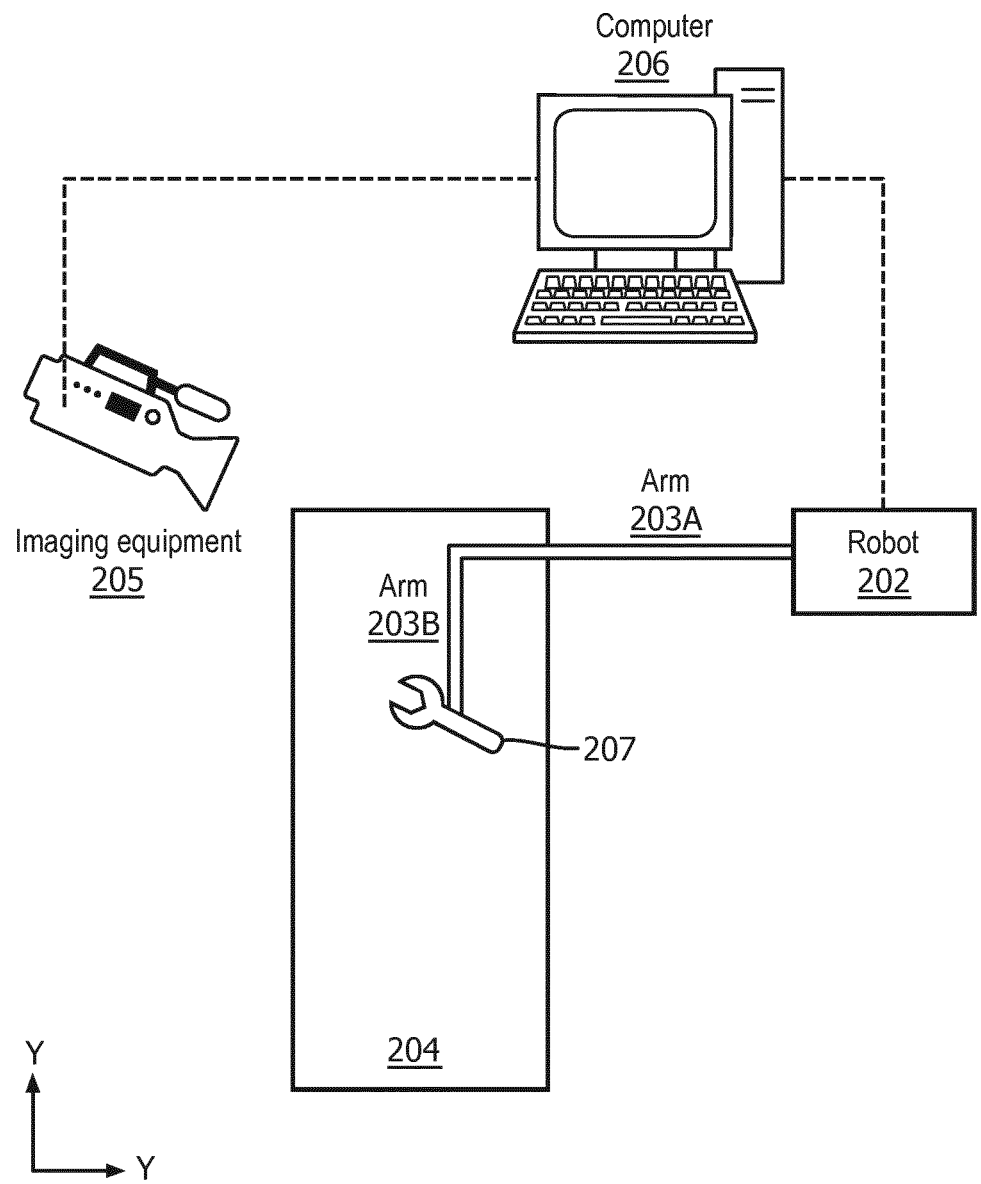
FIG. 2A illustrates a system for robotic tool control, in accordance with a representative embodiment.

FIG. 2A illustrates a system for robotic tool control, in accordance with a representative embodiment. In FIG. 2A, a structure 204 may be a bed or table such as an operating table. The 3-dimensional space around the structure 204 may be pre-mapped as described herein. Imaging equipment 205 may be a video camera, ultrasound device, X-ray device, or other devices that can capture images of a human organ and tissue during a medical operation.

The imaging equipment 205 feeds information from the captured images to computer 206. The computer 206 may store and execute motion tracking software that tracks motion of tissue in real time during the operation, so as to project a trajectory for a robotic tool 207 to meet the tissue. The robot 202 receives instructions from the computer 206, and manipulates arms 203A and 203B in three dimensions in order to move the robotic tool 207 to meet the tissue at an identified location and time. The manipulation of the arms 203A and 203B may be also be rotational. The manipulation of the arms 203A and 203B involves both moving the robotic tool 207 on the trajectory to meet the tissue, while also ensuring that the arms 203A and 203B and any other relevant components do not collide with the patient or any piece of equipment as a result of the trajectory of the robotic tool 207.

Though the computer 206 is described as performing most or all logical operations for the embodiment of FIG. 2, a robot 202 may directly perform all logical operations when the robot has appropriate mechanisms such as processors and memory for performing the logical operations. In an embodiment, the robot 202 and the computer 206 are part of a single integrated system. In another embodiment, the robot 202 and the computer 206 may be provided as a single subsystem. Logical operations include motion tracking of specified tissue, projections of future locations and times for the specified tissue based on the motion tracking, and trajectory setting of the robotic tool 207 based on the projections of future locations and times for the specified tissue.

The robot 202 described herein operates on the basis that continuous motion compensation may not be required, and instead integrates temporary but rapid observations of tissue motion into control strategy. The robot 202 therefore controls the arms 203A, 203B in accordance with the observations of tissue motion confirmation of a trajectory for the robotic tool 207. The tissue to be monitored can be set by the medical professional, and the trajectory defined or confirmed by the medical professional for the task to be performed. The location and time of the interception of the tissue in motion is determined in accordance with the timing of the tissue motion. The processing required to set the interception location and time may be invisible to the operator, so that the operator need only specify a tissue target, and the computer 206 computes the requisite trajectory and timing to execute the deployment. As a result, cognitive load on the medical professional is reduced and the operation is simplified. The computer 206 does not need to follow the fast and abrupt motion of the tissue for an extended time, and may perform the processes described herein in as little time as it takes for a single heartbeat or a few heartbeats. Thus, the monitoring/tracking of tissue motion to identify patterns resulting from heartbeat and respiration may be considered analogous to gaiting. As described herein, the tracked motion can be used to project positions and corresponding times of the heart tissue, and to generate a trajectory for a robotic tool to intercept the heart tissue.

As the system uses heartbeat timing to time deployment of the robotic end effector, the surgical system must also decide what position the tissue should be in when the deployment occurs so that the proper trajectory can be computed. The surgical system may consider various parameters in making this decision, including when the tissue is traveling slowest, fastest, at a directional extreme, and so on. Calculation of the trajectory of the robotic tool 207 can take into account the mechanical/computational latency of the robot 202, as well as the probability of successful deployment in a given scenario.

In an embodiment, a robotic system may include an embedded sensing system that monitors tissue motion. The embedded sensing system may be or include a small ultrasound transducer, electrodes (cardiac mapping probe), or a force sensor as a few examples. Information from the sensing system can be used to generate a model of the tissue motion prior to the procedure, as well as to update the model in real-time, and/or combine the information with an external monitoring system. In FIG. 2A, such a sensing system is generally represented by the imaging equipment 205. Information from the sensing system may be used to distinguish different sub-stages of the tissue motion via non-cyclical or non-linear motion models. The robot 202 may ultimately control the arms 203A and 203B in real time in accordance with information from the sensing system, and the control may be performed via the computer 206 and/or robot 202 using a memory or statistical model to act according to each intraoperative situation.

In an embodiment, the robotic system may include a controller based on the robot 202 and/or the computer 206. That is, a memory that stores instructions and a processor that executes the instructions may be elements of a controller. Such a controller may be a subsystem of the robot 202 or the computer 206, or may be a distributed subsystem of both the robot 202 and/or the computer 206, and even of another apparatus such as a remote computer that partially executes instructions. The instructions executed by a controller are used to perform some or all of the processes described herein for robotic tool control, including the processes of FIGS. 1 and 8 described herein.

Figure 2B:
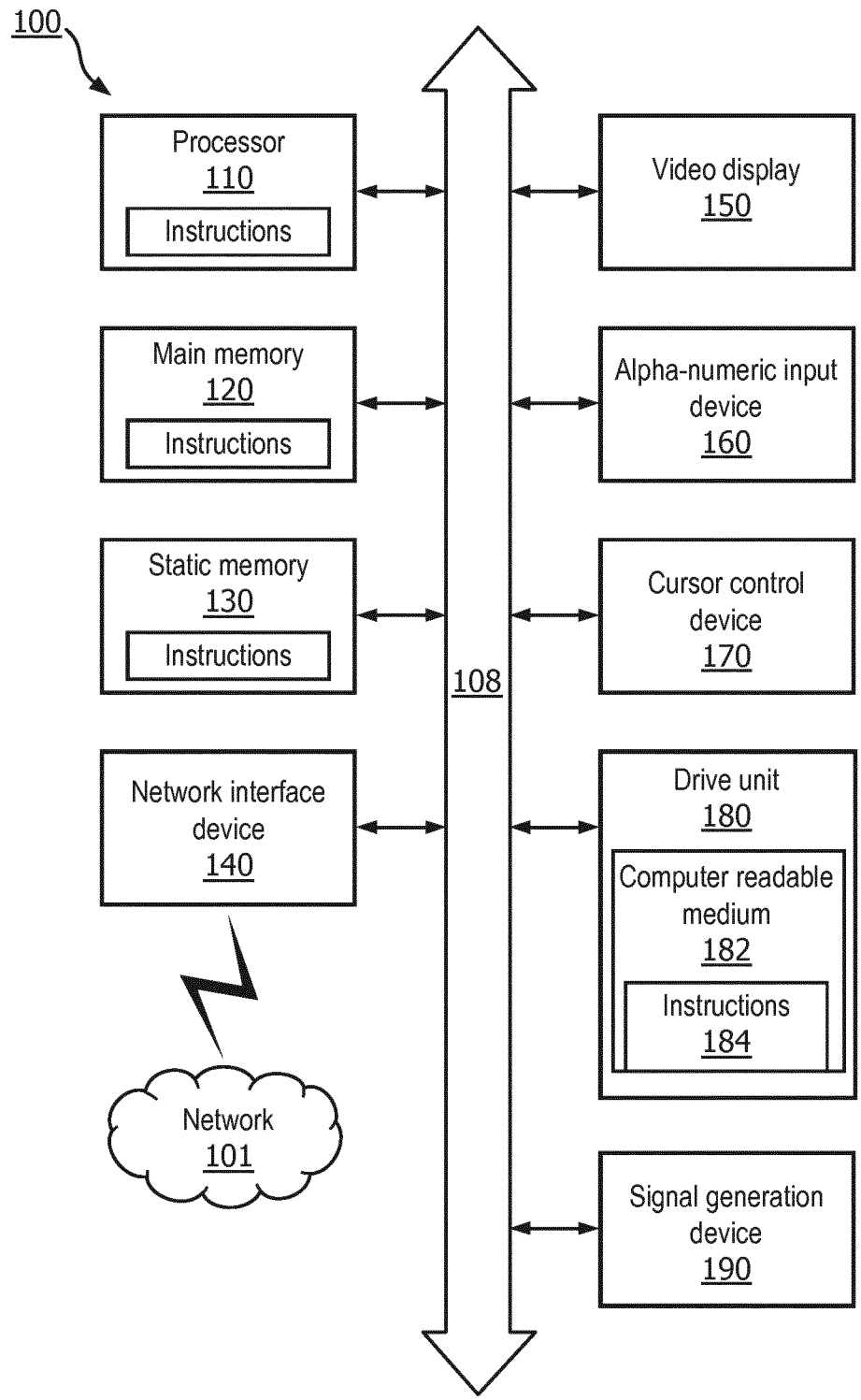
FIG. 2B illustrates a general computer system that includes a set of instructions for robotic tool control, in accordance with a representative embodiment.

FIG. 2B illustrates a general computer system that includes a set of instructions for robotic tool control, in accordance with a representative embodiment. FIG. 2B is an illustrative embodiment of a general computer system, on which a method of robotic tool control can be implemented, and which is shown and is designated 200. The computer system 200 can include a set of instructions that can be executed to cause the computer system 200 to perform any one or more of the methods or computer based functions disclosed herein. The computer system 200 may operate as a standalone device or may be connected, for example, using a network 201, to other computer systems or peripheral devices.

In a networked deployment, the computer system 200 may operate in the capacity of a server or as a client user computer in a server-client user network environment, or as a peer computer system in a peer-to-peer (or distributed) network environment. The computer system 200 can also be implemented as or incorporated into various devices, such as a controller, a stationary computer, a mobile computer, a personal computer (PC), a laptop computer, a robot, a medical robot, a surgical robot, a robotic system, or any other machine or system capable of executing a set of instructions (sequential or otherwise) that specify actions to be taken by that machine. The computer system 200 can be incorporated as or in a device that in turn is in an integrated system that includes additional devices. In an embodiment, the computer system 200 can be implemented using electronic devices that provide voice, video or data communication. Further, while a single computer system 200 is illustrated, the term "system" shall also be taken to include any collection of systems or sub-systems that individually or jointly execute a set, or multiple sets, of instructions to perform one or more computer functions.

As illustrated in FIG. 2B, the computer system 200 includes a processor 210. A processor for a computer system 200 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. A processor for a computer system 200 is configured to execute software instructions to perform functions as described in the various embodiments herein. A processor for a computer system 200 may be a general-purpose processor or may be part of an application specific integrated circuit (ASIC). A processor for a computer system 200 may also be a microprocessor, a microcomputer, a processor chip, a controller, a microcontroller, a digital signal processor (DSP), a state machine, or a programmable logic device. A processor for a computer system 200 may also be a logical circuit, including a programmable gate array (PGA) such as a field programmable gate array (FPGA), or another type of circuit that includes discrete gate and/or transistor logic. A processor for a computer system 200 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 200 includes a main memory 220 and a static memory 230 that can communicate with each other via a bus 208. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 200 may further include a video display unit 250, such as a liquid crystal display (LCD), an organic light emitting diode (OLED), a flat panel display, a solid-state display, or a cathode ray tube (CRT). Additionally, the computer system 200 may include an input device 260, such as a keyboard/virtual keyboard or touch-sensitive input screen or speech input with speech recognition, and a cursor control device 270, such as a mouse or touch-sensitive input screen or pad. The computer system 200 can also include a disk drive unit 280, a signal generation device 290, such as a speaker or remote control, and a network interface device 240.

In an embodiment, as depicted in FIG. 2B, the disk drive unit 280 may include a computer-readable medium 282 in which one or more sets of instructions 284, e.g. software, can be embedded. Sets of instructions 284 can be read from the computer-readable medium 282. Further, the instructions 284, when executed by a processor, can be used to perform one or more of the methods and processes as described herein. In an embodiment, the instructions 284 may reside completely, or at least partially, within the main memory 220, the static memory 230, and/or within the processor 210 during execution by the computer system 200.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 282 that includes instructions 284 or receives and executes instructions 284 responsive to a propagated signal; so that a device connected to a network 201 can communicate voice, video or data over the network 201. Further, the instructions 284 may be transmitted or received over the network 201 via the network interface device 240.

Figure 3:
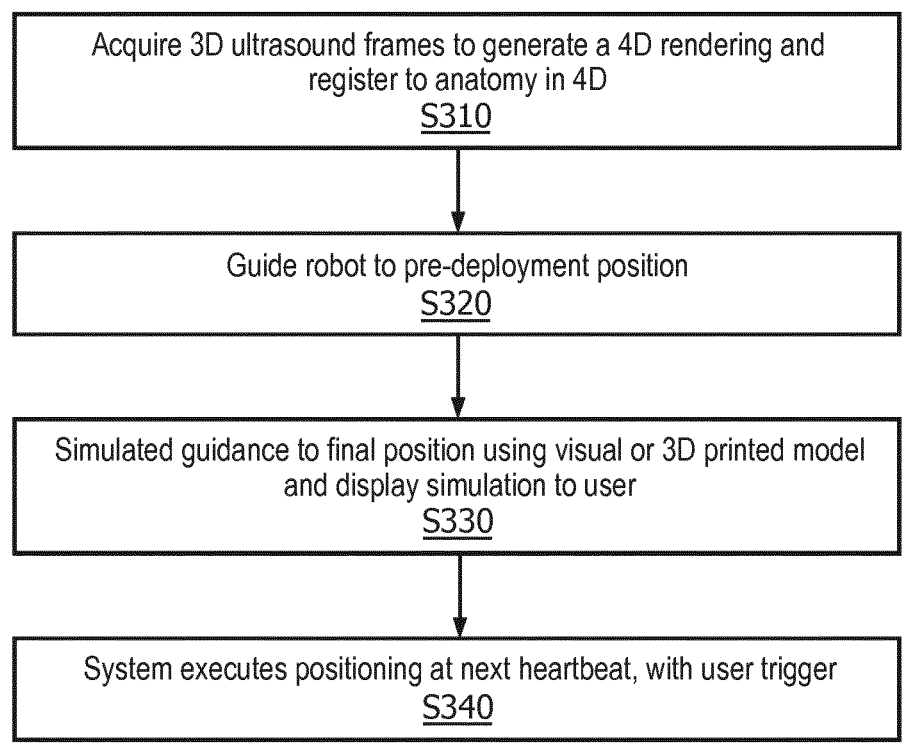
FIG. 3 illustrates another process for robotic tool control, in accordance with a representative embodiment.

FIG. 3 illustrates another process for robotic tool control, in accordance with a representative embodiment. The process in FIG. 3 starts at S310 by acquiring 3D ultrasound frames to generate a 4-dimensional rendering. The 4-dimensional rendering is also registered to the anatomy of a patient who is subject to a medical operation. In other words, at S310, a 4-dimensional rendering of the heart is generated from preoperative images, e.g., a temporal series of 3-dimensional ultrasound images. This rendering is registered to a patient model, intraoperative imaging, and the robot. S310 is not a necessary component of the control system itself, but inclusion of S310 adds to the overall usability of the robotic system.

At S320, a robot is guided to a pre-deployment position. The robot may be guided to a pre-deployment position by hand or by an automated process as described above. By hand, the robot may be guided close to a particular organ of the patient according to the judgement of the medical professional controlling the robot. By an automated process, the robot may be guided to a default position in a controlled area around the patient, such as a position above the foot of an operating table that holds the patient. In other words, at S320 the medical professional and/or the robot 202 guides the robot to a coarse pre-deployment position near the targeted site, e.g. the mitral valve. This part of the navigation is simpler than the intracardiac phase, so precise coordination between the monitored heart movement and the trajectory of the robotic tool is not yet necessary.

At S330, a simulation of the robot 202 being guided to a final position is generated visually or using a 3D printed model, and the simulation is then displayed to the medical professional controlling the robot. In an embodiment, multiple simulations may be generated and displayed, so that the medical professional can choose a simulation to use. The medical professional may also be provided an option to choose from an automated model or to manually guide the robotic tool with constraints imposed by the surgical system. The simulation may show a trajectory of a robotic tool from the pre-deployment position to the targeted tissue. The 3-dimensional space that includes the pre-deployment position and the operating range of the robot or a relevant part of the operating range may be mapped in advance using images, and images dynamically obtained for the operation may be merged to show context of the patient anatomy. The 3-dimensional ultrasound frames acquired at S310 are examples of images dynamically obtained for the operation, but other forms of imagery may also be used to provide context of a specific patent relative to a pre-mapped 3-dimensional space used for operations. In other words, at S330 the medical professional indicates via pre-operative and intraoperative imaging displays the desired anatomical location for the robot to target. A simulation of the robot motion can be optionally shown together with the predicted tissue motion. The medical professional may confirm or readjust the target as desired.

At S340, the system executes positioning at the next heartbeat, with a user trigger. By way of explanation, the patient in the operation is closely monitored with medical equipment, and the monitoring includes precise monitoring of heartbeat, as well as other relevant medical conditions such as respiratory functions. The robotic tool 207 being controlled is deployed based on the precise monitoring and in accordance with the trajectory shown in the simulated guidance at S330. In other words, since the heart moves in accordance with the heartbeat, respiratory function and other conditions, the movement of the heart is projected based on monitoring. Therefore, projected locations and corresponding times of the tissue are determined, and the trajectory shown in the simulated guidance is generated specifically to ensure the robotic tool or a device attached to the robotic tool meets the tissue at a projected location and time. Once confirmed, the robot system monitors the live tissue motion via intraoperative imaging, such as 3D ultrasound, or other forms of sensing, and matches the motion with the known motion model predicting the tissue motion. Once the tissue reaches a target position, the robot executes deployment of the end effector. This may involve grasping a leaflet or introducing a device into the tissue.

Figure 4:
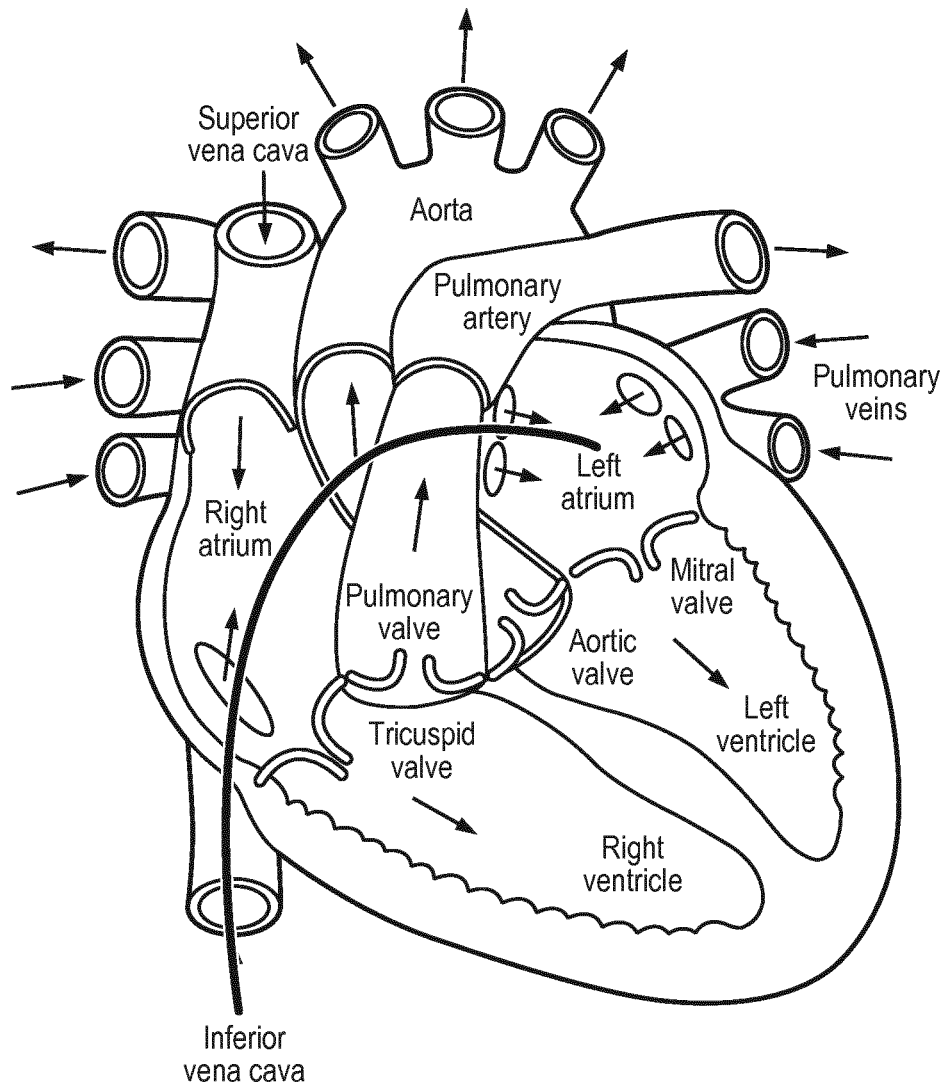
FIG. 4 illustrates a heart with tissue designated by an operator for robotic tool control, in accordance with a representative embodiment.
Figure 6:
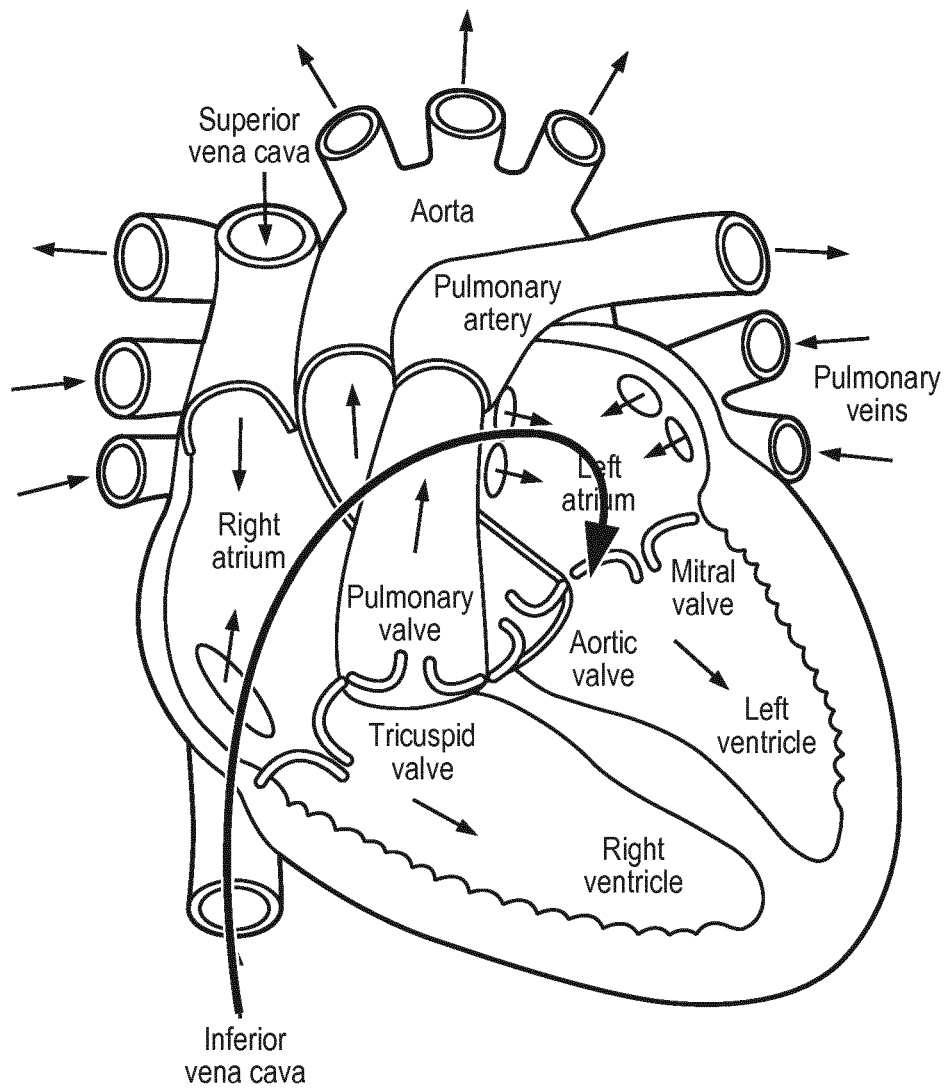
FIG. 6 illustrates the heart of FIG. 4 with the actual trajectory of a robotic tool for robotic tool control, in accordance with a representative embodiment.

FIG. 4 illustrates a heart with tissue designated by an operator for robotic tool control, in accordance with a representative embodiment. FIG. 4 illustrates S320, in that a trajectory is shown by which a robotic tool or therapy device is roughly guided to a location near a specific tissue of a heart that is the target. In FIGS. 4, 5 and 6, the heart is labelled with many different labelled corresponding to portions of the heart that would be recognized by medical professional. Insofar as any such portions of a heart are mentioned herein, the labels can be referenced to provide a generalized context for the discussion.

FIG. 5 illustrates the heart of FIG. 4 with a proposed trajectory of a robotic tool for robotic tool control, in accordance with a representative embodiment. FIG. 5 illustrates S330, in that simulated guidance to a final position of the specific tissue is generated and displayed to the user. The simulation in FIG. 5 is shown by the broken curve of the proposed trajectory, and the meeting location of the specific tissue and the robotic tool or therapy device is shown by an arrow.

FIG. 6 illustrates the heart of FIG. 4 with the actual trajectory of a robotic tool for robotic tool control, in accordance with a representative embodiment. FIG. 6 illustrates S340, in that the actual deployment of the robotic tool or therapy device is performed at the next heartbeat based on the user trigger. The user trigger is when the medical professional confirms the simulated guidance from S330. The next heartbeat is the heartbeat after the user trigger. Of course, the system may wait to, or tolerate, two or more heartbeats before deployment at S340 based on confirmation via the user trigger. However, since the simulation at S340 is precisely based on monitoring of the heart and medical conditions in real-time, the simulation will typically be ineffective after an extended time. Therefore, the language of the "next" heartbeat is intended to convey that the deployment of the robotic tool occurs quickly after the user confirms at S340 a trajectory simulated at S330.

The simulation at S330 may be updated rapidly and in real-time. For instance, the simulation of heart motion and the projected trajectory of the robotic tool or therapy device may be performed for every heartbeat, every 1 second, or even faster such as at every 0.1 second. On a monitor, the repeated performance of the simulation may be reflected in a refreshed image. The simulation will typically not change by a significant amount from one refresh to the next, but may change based on a sudden effect such as a non-rhythmic movement of the heart or even just a portion of the heart.

FIG. 7A illustrates a simplified form of tissue motion monitored in robotic tool control, in accordance with a representative embodiment. In FIG. 7A, motion of a heart is shown to be linear. Linear motion may still be reflected in changes in values in each of the X direction (horizontal), the Y direction (vertical) and the Z direction (depth), insofar as a linear movement will almost never be along a fixed axis for the X, Y or Z directions.

FIG. 7B illustrates another simplified form of tissue motion monitored in robotic tool control, in accordance with a representative embodiment. In FIG. 7B, motion of a heart appears to be purely rotational. However, rotational motion may also vary by radius from a center axis (or an origin) about which the rotation occurs. In FIG. 7C, the angles are designated as theta ($\Theta$) and phi ($\Phi$), where $\Theta$ is the angle in the XY plane and $\Phi$ is the angle in the YZ plane.

FIG. 7C illustrates another simplified form of tissue motion monitored in robotic tool control, in accordance with a representative embodiment. In FIG. 7C, rhythmic motion is shown as motion that occurs in segments that are retraced in at least one dimension of the XYZ scale in FIG. 7A. That is, motion in FIG. 7C may be back-and-forth retracing fully or partially in the X direction, Y direction and/or Z direction. Additionally, motion in FIG. 7C is rhythmic in a time component, in fully or partly repeating a pattern such as by hitting Y maximums and minimums at regular, periodic intervals.

Given the complexity of the human body and multiple functioning organs, motion of tissue of a heart may reflect multiple rhythms that overlap at the same time and in different directions. The result may appear chaotic visually at close inspection, but a rhythm or rhythms can be detected using motion tracking software that analyzes changes in location of the tissue of the heart over time. Moreover, motion analysis software may isolate linear or rotational motion(s) in addition to rhythmic motion(s). Once isolated, the motions can be projected forward in time to identify locations of the tissue of the heart at corresponding times in the (near) future.

Figure 8:
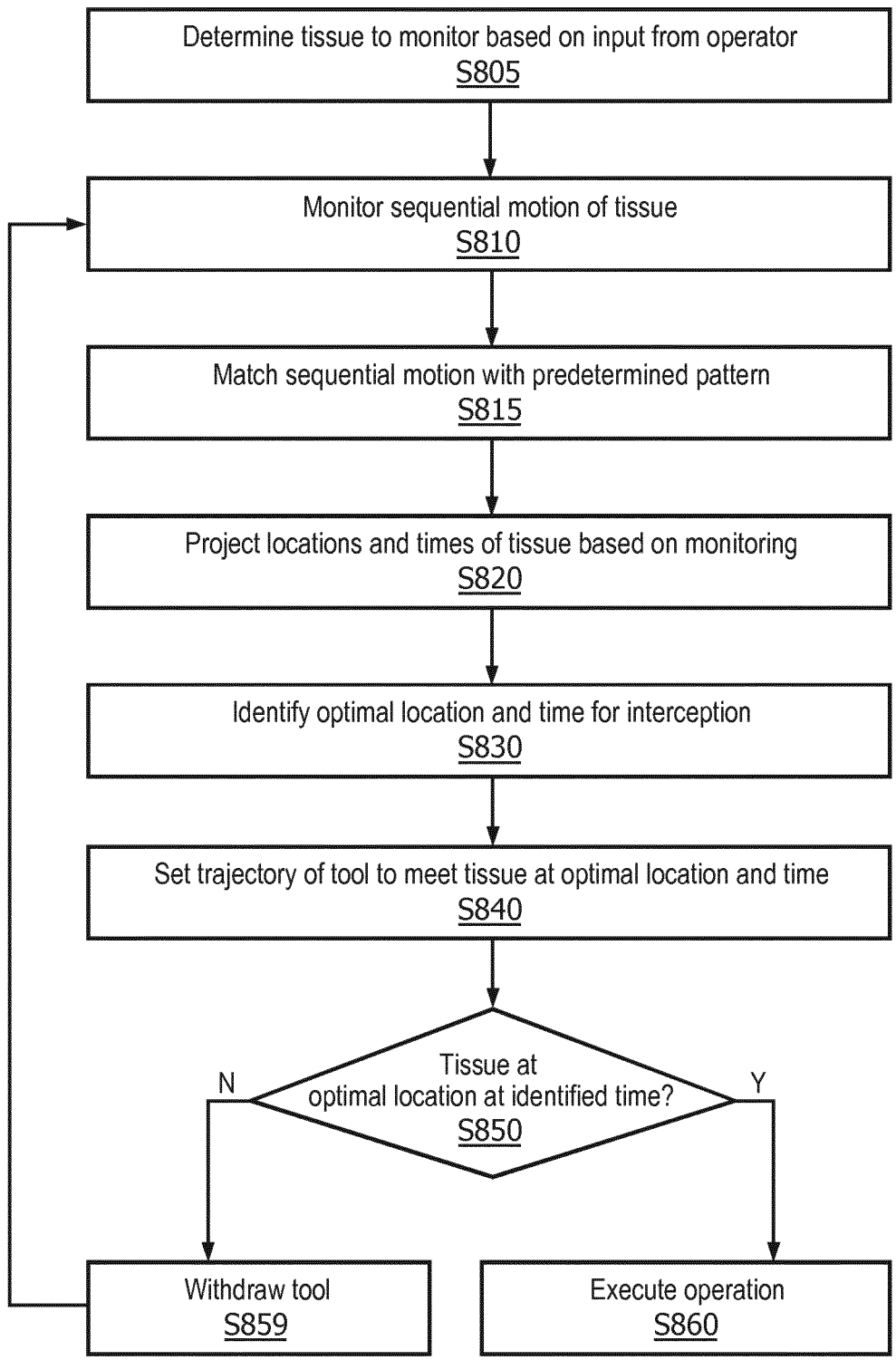
FIG. 8 illustrates another process for robotic tool control, in accordance with a representative embodiment.

FIG. 8 illustrates another process for robotic tool control, in accordance with a representative embodiment. In FIG. 8, the process starts at S805 by identifying tissue to monitor based on input from an operator. The tissue may be identified visually by the operator and then designated using an input device such as a mouse and cursor.

At S810, the identified tissue is monitored sequentially over time. That is, the identified tissue and surrounding tissue is monitored such as by images, for processing by motion analysis software.

At S815, sequential motion identified from the monitoring at S810 is matched with a predetermined pattern. For example, multiple predetermined patterns may be stored in a memory, and used to match motion identified from monitoring at S810. Each of the predetermined patterns may be associated with different labels, such as to designate when a pattern has been previously correlated with a type of medical condition.

At S820, locations and times of the heart tissue are projected based on the monitoring. The locations and times may be projected partly or entirely using the predetermined pattern matched at S815.

At S830, an optimal location and time for intercepting the tissue with the robotic tool or therapy tool are identified. Alternatively, an identified location and time may be preferred rather than optimal. That is, multiple locations and times that may be appropriate may be identified, and one may be designated by the medical professional or in accordance with predetermined settings. The identified location may thus be systematically optimal among a set of potential locations, or may be preferred such as when there is not clear optimal location.

At S840, a trajectory of the tool is set to meet the tissue at the optimal (or preferred) location and time. The trajectory may be a precise setting of positions of the tool at times in the future. The times for the multiple positions may be set at the level of milliseconds or even microseconds, and the positions of the robotic tool may be set as XYZ coordinates relative to an origin or as two RΘΦ coordinates relative to an origin.

At S850, a determination is made whether the tissue is at the optimal location and time. The determination may be made by motion tracking software or by a sensor that senses range, pressure/touch or electrical characteristics such as capacitance. If the tissue is not at the optimal location at the expected time (S850=No), the tool is withdrawn and the process is returned to S810 to repeat. If the tissue is at the optimal location at the expected time (S850=Yes), the operation is executed at S860. The operation may be inserting a needle, cutting the tissue, applying a therapy tool such as a mitral clip or valve, or other similar medical operation.

FIG. 9 illustrates data obtained from monitoring tissue motion in for robotic tool control, in accordance with a representative embodiment. In FIG. 9, twenty-five (25) times are shown sequentially at T1 to T25 in the first column. X values are shown as X1-X25 and are the X (axis) coordinate data values of the tissue as monitored at each of T1 to T25. Y values are shown as Y1-Y25 and are the Y (axis) coordinate data values of the tissue as monitored at each of T1 to T25. Z values are shown as Z1-Z25 and are the Z (axis) coordinate data values of the tissue as monitored at each of T1 to T25. R values are shown as R1-R25 and are the R (radius) data values of the tissue as monitored at each of T1 to T25. Θ values are shown as Θ1-Θ25 and are the Θ (angle in the XY plane) data values of the tissue as monitored at each of T1 to T25. Φ values are shown as Θ1-Φ25 and are the Φ (angle in the ZY plane) data values of the tissue as monitored at each of T1 to T25.

The data shown in FIG. 9 is therefore location data of specific tissue being monitored over time. The data is from tissue that is monitored to identify patterns such as linear, rotational and rhythmic motion. The patterns are then used to project optimal or preferred locations and times at which a robotic tool or therapy device may intercept the monitored tissue.

As described above, a surgical system allows a medical professional to robotically perform tasks on, or in the presence of, a moving object without having to cognitively take into account the motion in the decision-making process. The nature of the tasks and robot motion handled by the surgical system described herein is discrete, such that continuous robotic manipulation of a moving object is not required though it may still be present for other uses. The surgical system described herein can nonetheless be used to perform robotic task that use or previously used motion compensation, in that such task can be recast as a series of discrete robot deployments rather than continuous manipulation. The motion compensation problem previously used is replaced so that the system does not have to follow the motion of the tissue, and instead the system can pick salient situations for spot deployment, timing motion per a motion model. Where applicable, the approach provided by the robotic motion control described herein may be easier to implement and perform than straightforward motion compensation.

Although robotic tool control has been described with reference to several exemplary embodiments, it is understood that the words that have been used are words of description and illustration, rather than words of limitation. Changes may be made within the purview of the appended claims, as presently stated and as amended, without departing from the scope and spirit of robotic tool control in its aspects. Although robotic tool control has been described with reference to particular means, materials and embodiments, robotic tool control is not intended to be limited to the particulars disclosed; rather robotic tool control extends to all functionally equivalent structures, methods, and uses such as are within the scope of the appended claims.

As described above, even when tissue motion is in more than one degree of freedom, a surgical system may monitor the tissue and project locations and times of the tissue in advance. Such monitoring can be used to identify even complex patterns that account for actual motion of the tissue in multiple degrees of freedom. Therefore, the surgical system can operate even when the tissue motion is fast or abrupt, by dynamically, precisely and accurately deploying a robotic tool at a specific location and time determined in advance based on analysis of the tissue motion.

As described above, cardiac procedures such as mitral valve repair and patent foramen ovale closure can be performed using the surgical system described herein insofar as moving tissue does not have to be tracked or manipulated continuously for an extended period. The surgical system described herein has reduced reliance on motion compensation integrity, and can grasp at the target tissue to thereby secure the tissue for further manipulation. Alternatively, the robot may deploy a device that attaches to the target tissue. The surgical system described herein provides a robot that is required to accommodate heartbeat motion for as little as a single interval of time.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A controller for controlling a robotic tool, the controller comprising:
    a memory that stores instructions; and
    a processor coupled to the memory, the processor configured to:
        receive sensing signals of sensed tissue motion;
        monitor sequential motion of tissue in a three-dimensional space based on the sensing signals;
        project locations of the tissue in the three-dimensional space and corresponding times when the tissue will be at the projected locations;
        identify a location of projected locations;
        set a trajectory of the robotic tool to meet the tissue at the identified location at a projected time corresponding to the identified location; and
        send a control signal configured to control the robotic tool based on the trajectory.

2. The controller of claim 1, wherein the tissue is a heart and the sequential motion of the tissue is motion of at least one of a heartbeat, of a respiratory motion, and a feedback motion caused by the robot tool moving in response to the sequential motion of the tissue.

3. The controller of claim 1, wherein the processor is further configured to:
    determine the tissue based on input from an operator,
    select the identified location and the projected time corresponding to the identified location from a set of feasible locations and projected times corresponding to the feasible locations.

4. The controller of claim 1, wherein the processor is further configured to:
    match the sequential motion with a pattern among a set of predetermined patterns of sequential motion;
    project the locations and corresponding times based on the matched pattern; and
    withdraw the robotic tool in response to the tissue i-s-not being at the identified location at the corresponding projected time.

5. The controller of claim 1, wherein the sequential motion includes multiple rhythmic motions that overlap in different directions at a same time.

6. The controller of claim 1, wherein the processor is further configured to:
    obtaining a sequence of 3-dimensional images that include the tissue to monitor the sequential motion of the tissue.

7. A system for controlling a robotic tool, the system comprising:
    at least one of a sensor and an imaging system configured to sense tissue motion and generate sensing signals of the sensed tissue motion; and
    a processor configured to:
        receive the sensing signals of the sensed tissue motion;
        monitor sequential motion of tissue in a three-dimensional space based on the sensing signals;
        project locations of the tissue in the three-dimensional space and corresponding times when the tissue will be at the projected locations;
        identify a location of the projected locations; and set a trajectory of the robotic tool to meet the tissue at the identified location at a projected time corresponding to the identified location.

8. The system of claim 7, wherein the processor is further configured to:
obtain a sequence of 3-dimensional images that include the tissue to monitor the sequential motion of the tissue.

9. A method for controlling a robotic tool, the method comprising:
receiving sensing signals of sensed tissue motion;
monitoring sequential motion of tissue in a three-dimensional space based on the sensing signals;
projecting locations of the tissue in the three-dimensional space and corresponding times when the tissue will be at the projected;
identify a location of the projected locations and at least one characteristic of the robotic tool;
setting a trajectory of the robotic tool to meet the tissue at the identified location at a projected time corresponding to the identified location; and
controlling the robotic tool based on the trajectory.

10. The method of claim 9, further comprising:
obtaining a sequence of images that include the tissue to monitor the sequential motion of the tissue,
determining the tissue to be monitored based on the sequence of images, and
simulating the trajectory as a display to confirm or readjust the tissue to be monitored.

11. The method of claim 9, further comprising:
guiding the robotic tool to a pre-deployment position and then moving the robotic tool along the trajectory to meet the tissue at the identified location at the corresponding projected time from the pre-deployment position.

12. The method of claim 9, further comprising:
matching the sequential motion with a known motion model of a set of predetermined known motion models, and
identifying, from a plurality of feasible locations, the identified location at which the robotic tool or the a medical therapy device attached to the robotic tool will meet the tissue.

13. The method of claim 9, further comprising:
in a teleoperated deployment, moving the robotic tool towards the tissue based on input from an operator, and constraining motion of the robotic tool automatically based on the monitoring of the sequential motion of the tissue, or
in an autonomous deployment, moving the robotic tool towards the tissue based on determining the tissue to monitor, and autonomously executing deployment of the robotic tool by optimizing timing and trajectory.

14. The method of claim 9, further comprising:
identifying, from a set of possible characteristics for an optimal location, a characteristic to use to identify the identified location at which the robotic tool or a medical therapy device attached to the robotic tool will meet the tissue.

15. The method of claim 9,
wherein the identified location of the tissue is identified based on at least one of range sensing, pressure sensing, force sensing, electrical sensing, optical sensing, or imaging.

* * * * *